(12) United States Patent  
Michaelis

(10) Patent No.: US 11,657,779 B2  
(45) Date of Patent: May 23, 2023

(54) TRANSMISSION OF SOLID COLOR IMAGES OVER A COMMUNICATION SESSION FOR ILLUMINATION AT AN ENDPOINT

(71) Applicant: Avaya Management L.P., Durham, NC (US)

(72) Inventor: Paul Roller Michaelis, Louisville, CO (US)

(73) Assignee: Avaya Management L.P., Durham, NC (US)

( * ) Notice: Subject to any disclaimer, the term of this patent is extended or adjusted under 35 U.S.C. 154(b) by 0 days.

(21) Appl. No.: 17/392,617

(22) Filed: Aug. 3, 2021

(65) Prior Publication Data

US 2023/0040822 A1    Feb. 9, 2023

(51) Int. Cl.
*G09G 5/02*    (2006.01)
*G16H 80/00*   (2018.01)
*A61B 5/00*    (2006.01)
*G16H 40/67*   (2018.01)
*H04N 7/14*    (2006.01)

(52) U.S. Cl.
CPC ............... *G09G 5/02* (2013.01); *A61B 5/742* (2013.01); *G16H 40/67* (2018.01); *G16H 80/00* (2018.01); *H04N 7/147* (2013.01); *G09G 2320/062* (2013.01); *G09G 2320/0626* (2013.01); *G09G 2320/0666* (2013.01)

(58) Field of Classification Search
CPC ............... G09G 5/02; G09G 2320/062; G09G 2320/0626; G09G 2320/0666; G09G 2320/0693; G06T 2207/30204; G16H 40/67; G16H 80/00; H04N 7/147; A61B 5/742; A61B 5/339; A61B 5/375; A61B 5/486

See application file for complete search history.

(56) References Cited

U.S. PATENT DOCUMENTS

| | | | |
|---|---|---|---|
| 8,248,454 B2 * | 8/2012 | Thielman | H04N 17/02 348/14.07 |
| 9,042,967 B2 | 5/2015 | Dacosta et al. | |
| 9,088,689 B2 * | 7/2015 | Navon | H04N 7/142 |
| 10,692,599 B2 | 6/2020 | Hyde et al. | |
| 10,911,748 B1 * | 2/2021 | Molholm | H04N 17/04 |
| 2007/0216772 A1 * | 9/2007 | Xu | H04N 17/02 348/E9.051 |

* cited by examiner

*Primary Examiner* — Antonio A Caschera

(57) ABSTRACT

Controlling the illumination at an endpoint to a communication session by transmitting, over the communication session, the color of the light to be emitted by the display of the receiving endpoint. In a particular embodiment, a method includes, during a video communication session between a first endpoint operated by a first user and a second endpoint operated by a second user, transmitting first video, comprising a solid color image, from the first endpoint to the second endpoint over the video communication session, wherein the first video is prominently displayed at the second endpoint. At the first endpoint, the method provides receiving second video from the second endpoint. The second video is captured at the second endpoint while the first video is being displayed at the second endpoint. The method also includes displaying the second video to the first user.

20 Claims, 12 Drawing Sheets

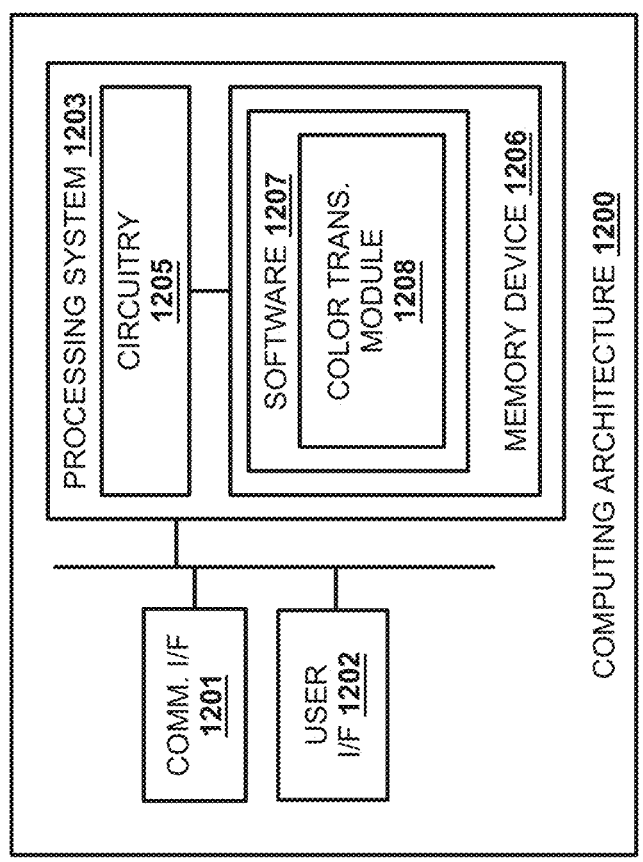

US 11,657,779 B2

TRANSMISSION OF SOLID COLOR IMAGES OVER A COMMUNICATION SESSION FOR ILLUMINATION AT AN ENDPOINT

TECHNICAL BACKGROUND

Items of interest can be difficult to detect visually when the items and the light illuminating them are the same or similar color. Items are more likely to be visually evident when illuminated by light that is a complementary color. The aforementioned properties can be used by physicians when diagnosing patients. For example, under broad spectrum lighting with a peak color temperature at 2700 degrees Kelvin (the typical color temperature of an incandescent bulb), a physician might fail to detect jaundice in a patient because, with that type of yellowish illumination, the inappropriately yellowish sclera of a jaundice patient's eyes and the white sclera of a healthy patient's eyes would both appear to be yellowish. On the other hand, if illuminated by broad spectrum light that has a peak color temperature closer to 5500 degrees Kelvin (the approximate color temperature of natural daylight), the sclera of the jaundice patient will still appear to be yellowish but the sclera of a healthy patient will appear to be white. While controlling the lighting may be relatively easy when both physician and patient are in the same location (e.g., the physician's exam room), the same cannot be said for the lighting at the patient's location during a remote video communication session between the physician and the patient (e.g., during a Telehealth appointment).

SUMMARY

The technology disclosed herein enables control of the illumination at an endpoint to a communication session by transmitting, over the communication session, the color of the light to be emitted by the display of the receiving endpoint. In a particular embodiment, a method includes, during a video communication session between a first endpoint operated by a first user and a second endpoint operated by a second user, transmitting first video, comprising a solid color image, from the first endpoint to the second endpoint over the video communication session, wherein the first video is prominently displayed at the second endpoint. At the first endpoint, the method provides receiving second video from the second endpoint. The second video is captured at the second endpoint while the first video is being displayed at the second endpoint. The method also includes displaying the second video to the first user.

In some embodiments, the method includes instructing the second endpoint to display the solid color image in a full screen mode.

In some embodiments, the method includes instructing the second endpoint to adjust a display brightness level.

In some embodiments, the method includes, at the first endpoint, receiving a selection of a color for the solid color image. In those embodiments, receiving the selection of the color may include displaying a color pallet to the first user, wherein the color is selected from the color pallet, or may include receiving a selection of a peak color temperature for full-spectrum light.

In some embodiments, the solid color image replaces a video image captured of the first user in the first video.

In some embodiments, the method includes instructing the second endpoint to disable display color adjustment.

In some embodiments, the method includes determining a type of video display and a type of video capture component at the second endpoint and adjusting display of the second video based on the type of video display and the type of video capture component.

In some embodiments, the method includes transmitting audio captured of the first user to the second endpoint with the first video.

In another embodiment, an apparatus is provided having one or more computer readable storage media and a processing system operatively coupled with the one or more computer readable storage media. Program instructions stored on the one or more computer readable storage media, when read and executed by the processing system, direct the processing system to, during a video communication session between a first endpoint operated by a first user and a second endpoint operated by a second user, transmit first video, comprising a solid color image, from the first endpoint to the second endpoint over the video communication session. The first video is prominently displayed at the second endpoint. At the first endpoint, the program instructions direct the processing system to receive second video from the second endpoint, wherein the second video is captured at the second endpoint while the first video is being displayed at the second endpoint, and display the second video to the first user.

BRIEF DESCRIPTION OF THE DRAWINGS

FIG. 12 illustrates a computing architecture for transmitting a color over a communication session for illumination at an endpoint.

DETAILED DESCRIPTION

During a two-way video telecommunication session between two users, one user's endpoint generates and transmits a solid color image via a video channel of the communication session. The other endpoint receives the video transmission and displays the image to its user. The light emitted by the display of the receiving endpoint, and therefore the solid color that was transmitted, illuminate the space at the receiving endpoint. Preferably, other light sources at the receiving endpoint are eliminated or minimized. The image of the user who is being illuminated in this manner is transmitted to the other user. Advantageously, when a user on the color-transmitting end of a communication session desires to detect or examine something that is more discernible when illuminated by a specific color of light, the user can transmit the color that will produce those lighting conditions at the location of the receiving endpoint. In a practical example, a physician on a Telehealth session with a patient may visually diagnose a patient based on what they are able to see when their patent is illuminated by a particular color. Illustratively, the presence of jaundice would be difficult to detect in a Telehealth session if the patient is illuminated with yellow light, but would be much more apparent to the physician if the patient is illuminated with white or purple light.

Figure 1:
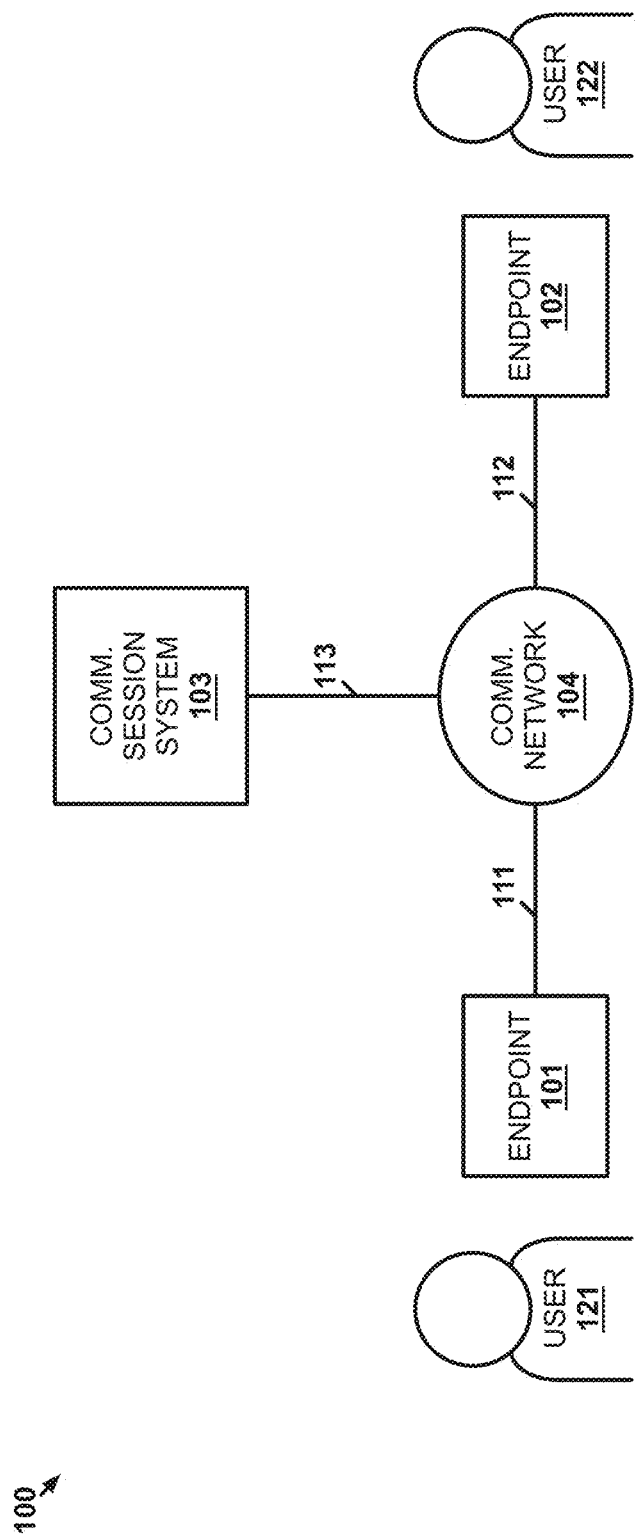
FIG. 1 illustrates an implementation for transmitting a color over a communication session for illumination at an endpoint.

FIG. 1 illustrates implementation 100 for transmitting a color over a communication session for illumination at an endpoint. Implementation 100 includes endpoint 101, endpoint 102, communication session system 103, and communication network 104. User 121 operates endpoint 101 and user 122 operates endpoint 102. Communication network 104 includes one or more local area networks and/or wide area computing networks, such as the Internet. Endpoint 101, endpoint 102, and communication session system 103 communicate with communication network 104 over communication links 111-113, respectively. Communication links 111-113 are shown as direct links but may include intervening systems, networks, and/or devices.

In operation, endpoint 102 and endpoint 103 may each respectively be a video-capable telephone, tablet computer, laptop computer, desktop computer, conference room system, or some other type of computing device capable of connecting to a communication session facilitated by communication session system 103. Communication session system 103 facilitates communication sessions between two or more endpoints, such as endpoint 101 and endpoint 102. In some examples, communication session system 103 may be omitted in favor of a peer-to-peer communication session between endpoint 101 and endpoint 102. A communication session includes at least a video channel between endpoint 101 and endpoint 102 but may also include an audio channel (e.g., for voice communications), a graphic component (e.g., presentation slides, screen sharing, etc.), text chat component, and/or some other type of real-time communication. Other examples may include more than two participants and/or more than two endpoints on the communication session.

Figure 2:
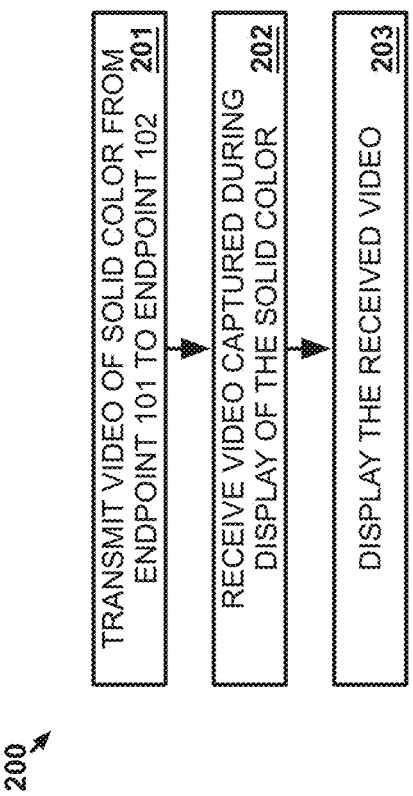
FIG. 2 illustrates an operation to transmit a color over a communication session for illumination at an endpoint.

FIG. 2 illustrates operation 200 to transmit a color over a communication session for illumination at an endpoint. In operation 200, a video communication session facilitated by communication session system 103 has been established between endpoint 101 and endpoint 102. The communication session features a video channel that transmits real-time video from endpoint 101 to endpoint 102 and from endpoint 102 to endpoint 101. Traditionally, the video channel may be used to transmit real-time video captured of respective users 121 and 122 (e.g., a video call or video conference). In this example, as described below, a solid color image is transmitted instead of other real-time video, or no video at all (e.g., when user 121 has their camera disabled/muted for the session), from endpoint 101 to endpoint 102. The communication session may also have an audio channel that allows user 121 and user 122 to speak to each other in real time. Although, user 121 and user 122 may exchange words in some other manner (e.g., may use separate telephone devices to speak over a voice call contemporaneously to the communication session). Endpoint 101 and endpoint 102 may each execute a communication client application for participating in video communication sessions. The communication client may be installed directly on endpoint 101/102 or may execute through another application, such as a web browser.

During the video communication session, endpoint 101 transmits video, comprising a solid color image, to endpoint 102 (201). The image is a solid color because substantially all of the image is one color. Since the image is transmitted as video over the communication session, the solid color image is used for each frame of the video so that the image is consistent when the video is displayed at endpoint 102. A frame with the solid color image may include pixels that all, or the vast majority, are the same color. The color may be a distinct color on the visible color spectrum that is supported by endpoint 101 and endpoint 102 (e.g., various hues of red, green, blue, yellow, etc.) or may be a broad-spectrum color defined by its peak color temperature (commonly represented in degrees Kelvin (K)). For example, an incandescent lightbulb usually has a peak color temperature around 2,700K. It should be understood that each pixel in many types of displays includes sub-pixels of different colors (e.g., a red, a green, and a blue sub-pixel) that are lit in varying intensities to produce additional colors (e.g., yellow, orange, etc.). Similarly, groups of pixels may be used to produce a certain color. In some examples, the color may be selected, or otherwise defined, by user 121 though a user interface of endpoint 101. Upon receiving the video, the video is displayed at endpoint 102. Preferably, the video is displayed prominently so that most of the illumination from a display of endpoint 102 comes from the solid color image. The prominent display may stem from the video taking up a large portion of the display screen, from the video taking up the entire display screen (e.g., "full screen" mode), from display elements other than the video being darker than the video (e.g., greyed out), from brightness levels of the display screen around the video being brighter than those of other areas of the display screen, or some other manner in which the video can be displayed to be a primary source of light from the display—including combinations thereof. Preferably, endpoint 102 is located in a dark, or minutely lit, area so that colors from light sources other than the displayed solid color image do not interfere with the light produced by endpoint 102.

In some examples, endpoint 101 may be able to control how the video is displayed at endpoint 102. For example, endpoint 101 may control the brightness of endpoint 102's display, may direct endpoint 102 to display the video in a particular window size or in full screen, may adjust settings (e.g., disable or otherwise modify white balance or other color adjustments) of the display to ensure the color is displayed properly in the video, or may control the display in some other manner. The control may be performed by endpoint 101 sending a control message to endpoint 102 and endpoint 102, responsively, using one or more Application Programming Interfaces (APIs) of endpoint 102's operating system, such as a window management API, to comply with the control message. In addition, endpoint 101 may control the camera and other image transmission components of endpoint 102, such as the focus, brightness, white balance, and color settings.

While the video is being displayed at endpoint 102, endpoint 102 captures video via a camera for transmission to user 121 in real time over the video communication session. Preferably the camera is directed to capture images in substantially the same direction as the display of the solid color image is pointed so that anything captured by the camera is illuminated by the solid color image. In many modern user systems, such as a smartphone, tablet or laptop, a camera is built into a display housing that forces the display and the camera to be pointed in the same direction. In a Telehealth example, user 122 is positioned in front of the display of user 122 and the camera of user 122 is pointed at user 122 for communicating with user 121. Thus, the display of the solid color image illuminates user 122 and video is captured of user 122 during that illumination.

In some examples, endpoint 101 may receive information about the display being used to display the video at endpoint 102 and/or the camera used to capture video at endpoint 102, or the settings thereof. Endpoint 101 may use the information to adjust the video of the solid color image before sending the video to ensure the desired illumination effect is achieved (i.e., the desired wavelengths are produced). The information may indicate a make and/or model of the display and/or camera, may indicate settings thereof, or may include other information that indicates to endpoint 101 that the video should be adjusted. In an example, the information may indicate to endpoint 101 that a particular type of display is used by endpoint 102 and endpoint 101 references records (either locally or elsewhere) that indicate the particular type of displays skews colors in a particular manner (e.g., presents more blue tones). Endpoint 101 may then adjust the video to compensate for the skew caused by the display type.

Endpoint 101 receives the captured video from the second endpoint (202) and displays the video to user 121 (203). The video may be received and displayed to user 121 in the same manner as video captured by endpoint 102 would even without displaying the solid color image (i.e., video captured when user 121 and user 122 are communicating through the exchange of real-time video captured of both users over the video communication session). For example, instead of user 122 viewing video captured of user 121 by endpoint 101 when endpoint 102 captures the video, endpoint 102 is displaying the solid color image. Although, to endpoint 102, the fact that the video includes the solid color image makes no difference because endpoint 102 displays whatever video is received from endpoint 101 regardless of what video images the video includes.

Advantageously, since the video captured by endpoint 102 is captured and presented by endpoint 101 to user 121 while endpoint 102 is displaying the solid color image, user 121 will be able to see things (if such things are present) at endpoint 102 that are more visible when illuminated in the color of the solid color image. For example, user 121 may be able to identify jaundice in user 122 when the solid color image is a color conducive to identifying jaundice in the eyes of user 122. While the examples above focus on a Telehealth type scenario, operation 200 may be used for reasons other than diagnosing patients remotely. Many different types of objects, living or otherwise, may include features that can be better seen under different lighting conditions. For instance, the presence of a blue-green mold (such as *Penicillium expansum*) on a white surface would be much more evident when illuminated by red light. Therefore, if a user wishes to view those features remotely, then operation 200 may be performed to provide desirable illumination characteristics.

Figure 3:
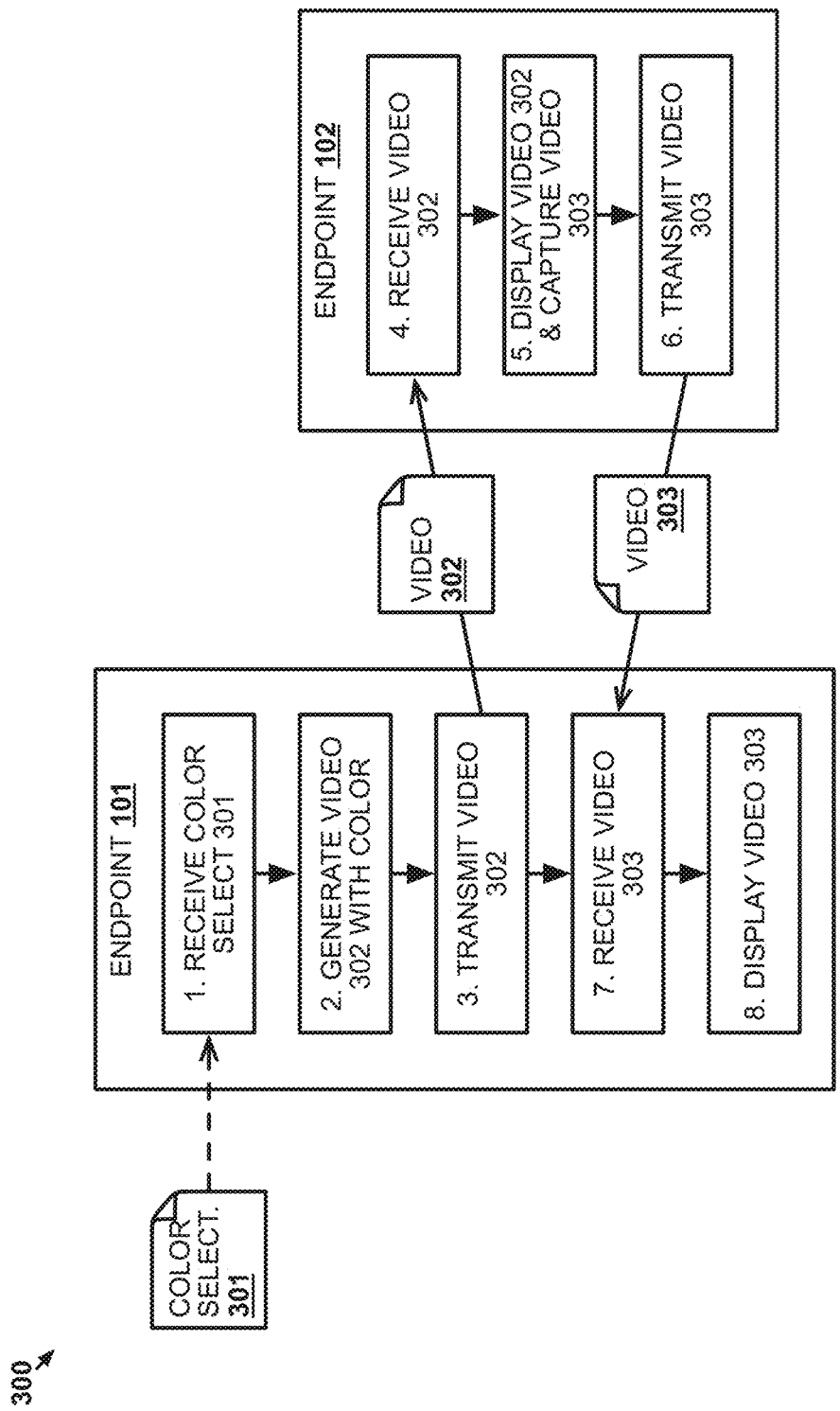
FIG. 3 illustrates an operational scenario for transmitting a color over a communication session for illumination at an endpoint.

FIG. 3 illustrates operational scenario 300 for transmitting a color over a communication session for illumination at an endpoint. Operational scenario 300 is an example where user 121 selects the color that will be displayed at endpoint 102 during the video communication session. At step 1, endpoint 101 receives color selection 301 from user 121. Color selection 301 may select a specific color or may define a peak color temperature for broad spectrum light produced by a color. Endpoint 101 may present user 121 with a color wheel, color spectrum slide bar, temperature slider, number entry box for color temperature, or some other graphical input element. In response to receiving color selection 301, endpoint 101 generates video 302 at step 2 with a solid color image of the color defined in color selection 301. The frames of video 302 are, therefore, made up of the solid color image rather than, for example, images captured of user 121. In some examples, the generated video 302 replaces video 302 captured of user 121 prior to receipt of color selection 301. Although, in some cases, a video component of the video communication session from endpoint 101 to endpoint 102 may be muted or otherwise is not being sent to and/or displayed at endpoint 102.

Video 302 is transmitted to endpoint 102 at step 4. At step 5, endpoint 102 displays video 302 and captures video 303. Endpoint 102 may already be capturing video 303 for the video communication session prior to the display of video 302 (e.g., for transmission to endpoint 101 so that user 122 can be seen by endpoint 101 prior to the solid color image being displayed) or endpoint 102 may begin capturing video 303 after receiving video 302. Endpoint 102 transmits video 303 to endpoint 101 at step 6. Endpoint 101 receives video 303 at step 7 and displays video 303 at step 8 to user 121. Since steps 2-8 occur continually in real time, user 121 is able to see user 122 in real time while endpoint 102 is illuminating user 122 via the display of video 302.

Endpoint 101 may continue to generate and send video 302 with the solid color image until user 121 instructs it to stop, until an amount of time has elapsed, until the video communication session is ended, or until some other condition is met. In some cases, upon endpoint 101 stopping the generation of video 302 with the solid color image, endpoint 101 may capture video of user 121 for transmission to endpoint 102 in video 302 in place of the solid color image. For example, user 121 may have seen everything they needed to while endpoint 102 was displaying the solid color image and then may want user 122 to see them while their conversation is continued.

Figure 4:
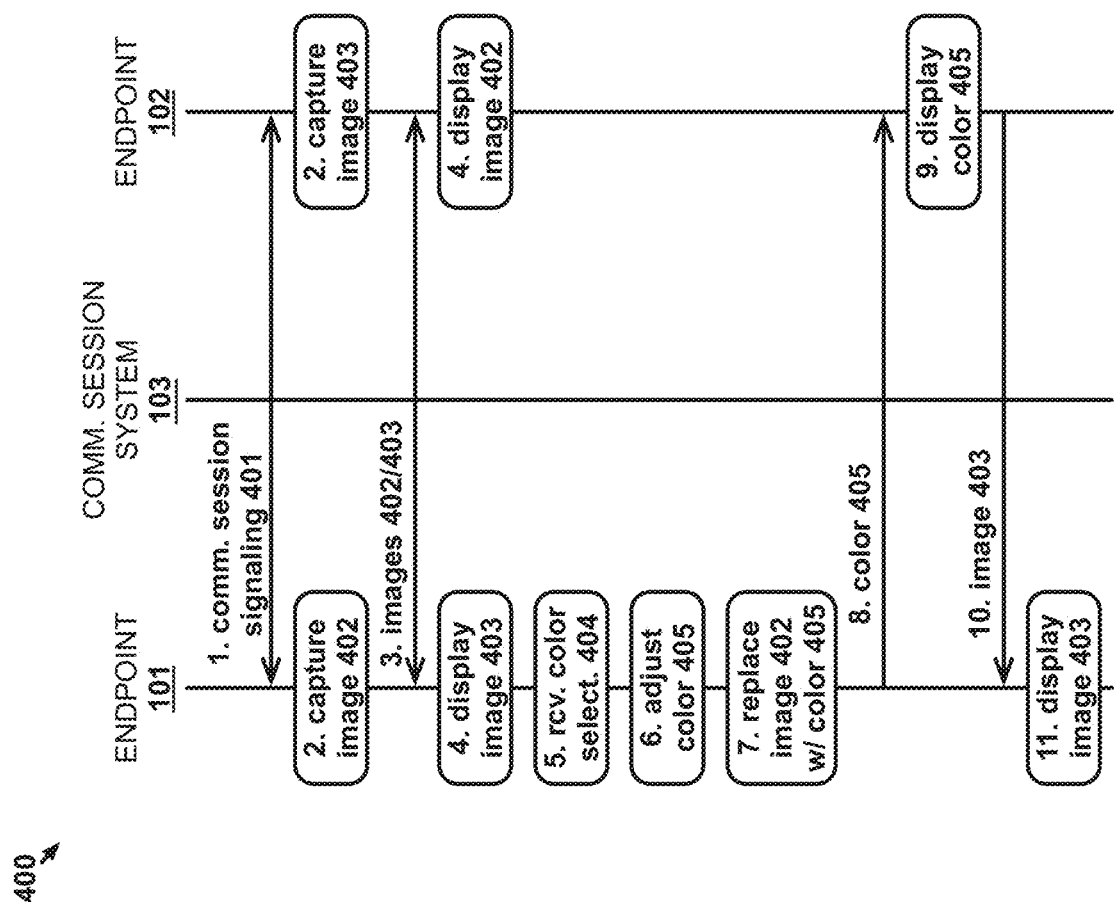
FIG. 4 illustrates an operational scenario for transmitting a color over a communication session for illumination at an endpoint.

FIG. 4 illustrates operational scenario 400 for transmitting a color over a communication session for illumination at an endpoint. Operational scenario 400 is an example of a video communication session between endpoint 101 and endpoint 102 from establishment of the session. In operational scenario 400, endpoint 101 and endpoint 102 exchange communication session signaling 401 to establish a real-time video communication session at step 1 between endpoint 101 and endpoint 102. The signaling may be Session Initiation Protocol (SIP) signaling, Web Real-Time Communications (WebRTC) signaling, h.323 signaling, or some other signaling protocol. The signaling may also be used to control image capture and/or display at endpoint 101 and/or endpoint 102 (e.g., endpoint 101 may use the signaling to adjust display brightness or camera white balance at endpoint 102). After establishing the video communication session, endpoint 101 and endpoint 102 begin exchanging real-time user communications captured from user 121 and user 122. In this example, the user communications include video and audio so that user 121 and user 122 can see and hear each other.

For the video component of the user communications, at step 2, endpoint 101 captures video images 402 and endpoint 102 capture video images 403. Video images 402 and video images 403 are image frames that, when played back, produce a video image. Video images 402 and video images 403 are then exchanged at step 3 over a video channel of the video communication session. At step 4, endpoint 101 displays video images 403 received from endpoint 102 and endpoint 102 displays video images 402 received from endpoint 101. Steps 2-4 continue unchanged until video images 402 are replaced with solid color image 405, as described below. Though not shown, endpoint 101 and endpoint 102 also capture audio from user 121 and user 122 and transmit the audio of an audio channel of the video communication session.

At step 5, endpoint 101 receives color selection 404 from user 121. Color Selection 404 indicates that solid color image 405 should be used for the video frames sent to endpoint 102 in place of video images 402. In this example, endpoint 101 determines that solid color image 405 should be adjusted to account for display and/or video capture aspects of endpoint 102. For instance, endpoint 101 may determine that the display of endpoint 102 has a particular white balance characteristic that can be accounted for by adjusting the color of solid color image 405. Endpoint 101 performs that adjustment at step 6. After adjusting solid color image 405, endpoint 101 replaces video images 402 with solid color image 405 at step 8. The frames of the video being transmitted over the video channel of the video communication session at step 8 are now solid color image 405 rather than video captured of user 121.

Video 302 displays solid color image 405 at step 9. While display of solid color image 405 is a distinct step, from the perspective of endpoint 102 the same video is still being displayed. It does not matter if the video includes video images 402 or solid color image 405, endpoint 102 simply displays what it receives. From the perspective of user 122, user 122 may see video images 402 switch to solid color image 405 while viewing the received video. Even as endpoint 101 is changing the video to include solid color image 405, endpoint 102 continues to capture video images 403 of user 122. As shown in step 10, the video including video images 403 continues to be transmitted to endpoint 101 in real time even as endpoint 102 is displaying the video having solid color image 405. Likewise, endpoint 101 continues to present video images 403 at step 11. From the perspective of user 121, video images 403 continue presentation as they were in step 4 but, at step 11, user 122 is now illuminated by solid color image 405. In some examples, endpoint 101 may instruct endpoint 102 to display the video in full screen, increase screen brightness, or otherwise enhance the light produced by endpoint 102, while solid color image 405 is included in the video. In some cases, endpoint 101 may further be able to direct other sources of light at endpoint 102's location (e.g., smart home lights) to turn off so as to not interfere with the light produced from the display of solid color image 405. Otherwise, user 121 may simply request over the video communication session that user 122 reduce the amount of light other than that produced by solid color image 405.

After user 122 has seen enough with user 122 illuminated by solid color image 405, user 121 may direct endpoint 101 to stop transmitting solid color image 405. Endpoint 101 may then revert to sending up to date video images 402 (e.g., endpoint 101 may restart capture of video images 402) so that user 121 and user 122 can continue their communication while seeing each other in real time. For example, user 121 may instruct endpoint 101 to send solid color image 405 to endpoint 102 for a period of time necessary for user 121 to diagnose user 122 and then switch back to normal video communications. Similarly, endpoint 101 may instruct endpoint 101 to change solid color image 405 during presentation to better fit the situation (e.g., to attempt to see something with better contrast than was allowed for with the initially selected solid color image 405).

In some examples, rather than endpoint 101 generating solid color image 405 itself and including solid color image 405 in the video transmitted to endpoint 102, communication session system 103 may be instructed to do so. For instance, after receiving color selection 404 at step 5, endpoint 101 may transmit a message to communication session system 103 that instructs communication session system 103 to generate solid color image 405 and include solid color image 405 in video transmitted endpoint 102. The video with solid color image 405 would still come from endpoint 101 from the perspective of endpoint 102 even though communication session system 103 generated solid color image 405. Since video images 402 are no longer being sent to endpoint 102, endpoint 101 may stop sending video images 402 in video to communication session system 103 during transmission of video with solid color image 405.

Figure 5:
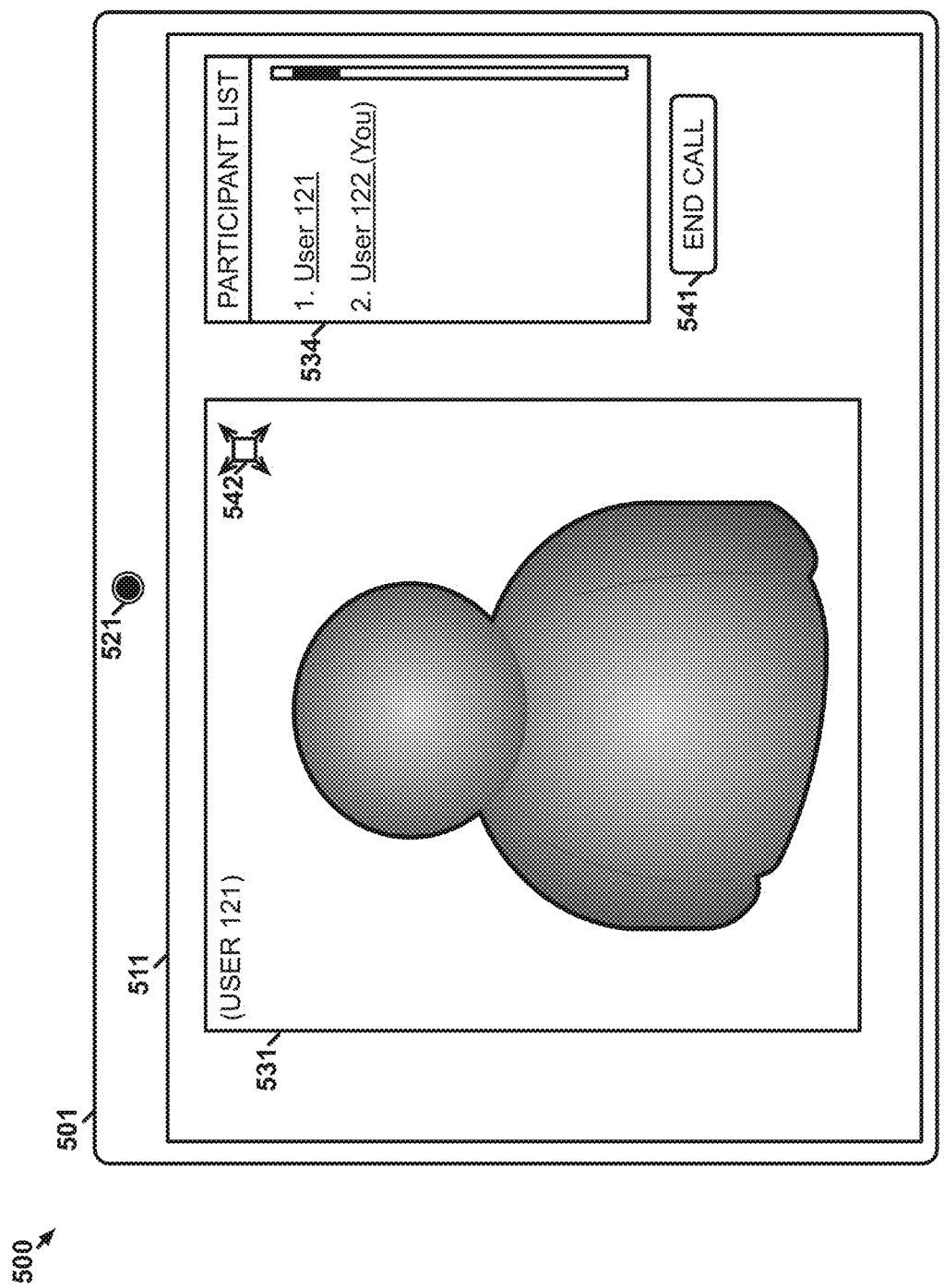
FIG. 5 illustrates an implementation for transmitting a color over a communication session for illumination at an endpoint.

FIG. 5 illustrates implementation 500 for transmitting a color over a communication session for illumination at an endpoint. Implementation 500 includes display system 501, which includes display screen 511 and camera 521. Display system 501 is a display system of endpoint 102. Display screen 511 may be a liquid crystal display (LCD), organic light emitting diode (OLED) display, cathode ray tube (CRT), or some other type of display in communication with processing circuitry of user system 102. Camera 521 includes optics, such as a lens, and an image sensor, also in communication with processing circuitry of a user system, that captured photos and/or video, which may be included in posts to communication channels. In some examples, display system 501 may further include a microphone and/or one or more speakers for user 122 to input and receive voice communications. In this example, the microphone and speakers are located elsewhere for endpoint 102 (e.g., built into a headset connected to endpoint 102).

In implementation 500, display screen 511 is displaying a graphical user interface for a client application executing on endpoint 102 for connecting to communication sessions facilitated by communication session system 103. In this example, endpoint 102 is currently connected to a video communication session with endpoint 101. Participant list window 534 lists the two participants on the video communication session, user 121 and user 122. Video session window 531 displays real-time video captured of user 121 by camera 621 (shown in implementation 600) and transmitted to endpoint 102 over the communication session. The video communication session also exchanges audio captured of user 121 and user 122 so that user 121 and user 122 can hear and see each other during a real time conversation over the video communication session. Should user 122 want the video from endpoint 101 to be displayed in full screen, user 122 may select full screen button 542. Should user 122 want to end the video communication session, user 122 may select end call button 541.

Figure 6:
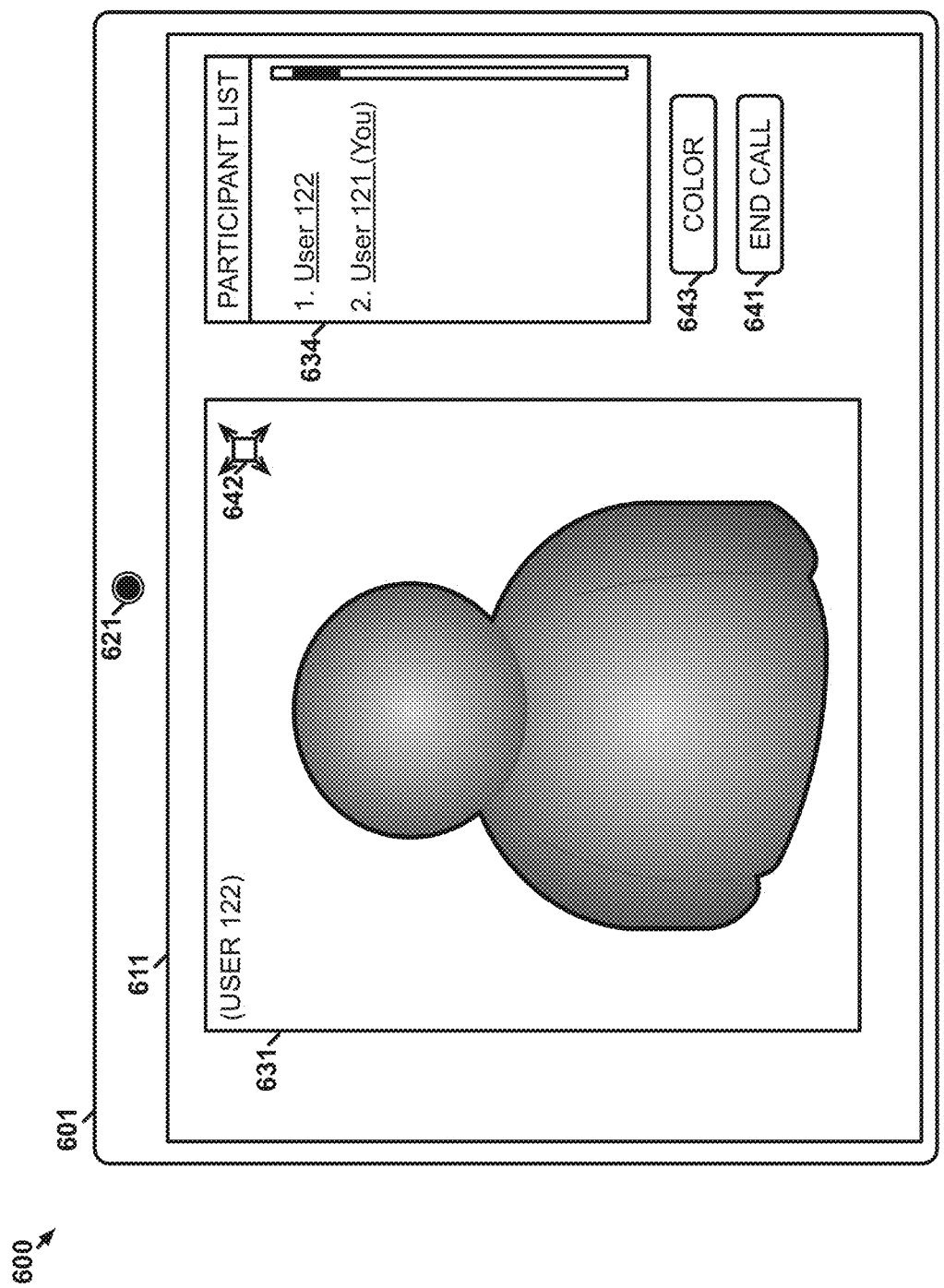
FIG. 6 illustrates an implementation for transmitting a color over a communication session for illumination at an endpoint.

FIG. 6 illustrates implementation 600 for transmitting a color over a communication session for illumination at an endpoint. Implementation 600 includes display system 601, which includes display screen 611 and camera 621. Display system 601 is a display system of endpoint 101. Display screen 611 may be a liquid crystal display (LCD), organic light emitting diode (OLED) display, cathode ray tube (CRT), or some other type of display in communication with processing circuitry of user system 102. Camera 621 includes optics, such as a lens, and an image sensor, also in communication with processing circuitry of a user system, that captured photos and/or video, which may be included in posts to communication channels. In some examples, display system 601 may further include a microphone and/or one or more speakers for user 121 to input and receive voice communications. In this example, the microphone and speakers are located elsewhere for endpoint 101 (e.g., built into a headset connected to endpoint 101).

In implementation 600, display screen 611 is displaying a graphical user interface for a client application executing on endpoint 101 for connecting to communication sessions facilitated by communication session system 103. In this example, endpoint 101 is currently connected to the video communication session with endpoint 102 mentioned above. Participant list window 634 lists the two participants on the video communication session, user 121 and user 122. Video session window 631 displays real-time video captured of user 122 by camera 521 and transmitted to endpoint 101 over the communication session. Should user 121 want the video from endpoint 101 to be displayed in full screen, user 121 may select full screen button 642. Should user 121 want to end the video communication session, user 121 may select end call button 641.

The client displayed by display screen 611 also includes color button 643, which user 121 may select when they want a solid color image to be transmitted in the video to endpoint 102 in place of video captured of user 121 by camera 621. In some examples, display screen 511 may also display a color button to allow user 122 to access the solid color image transmission features described below.

Figure 7:
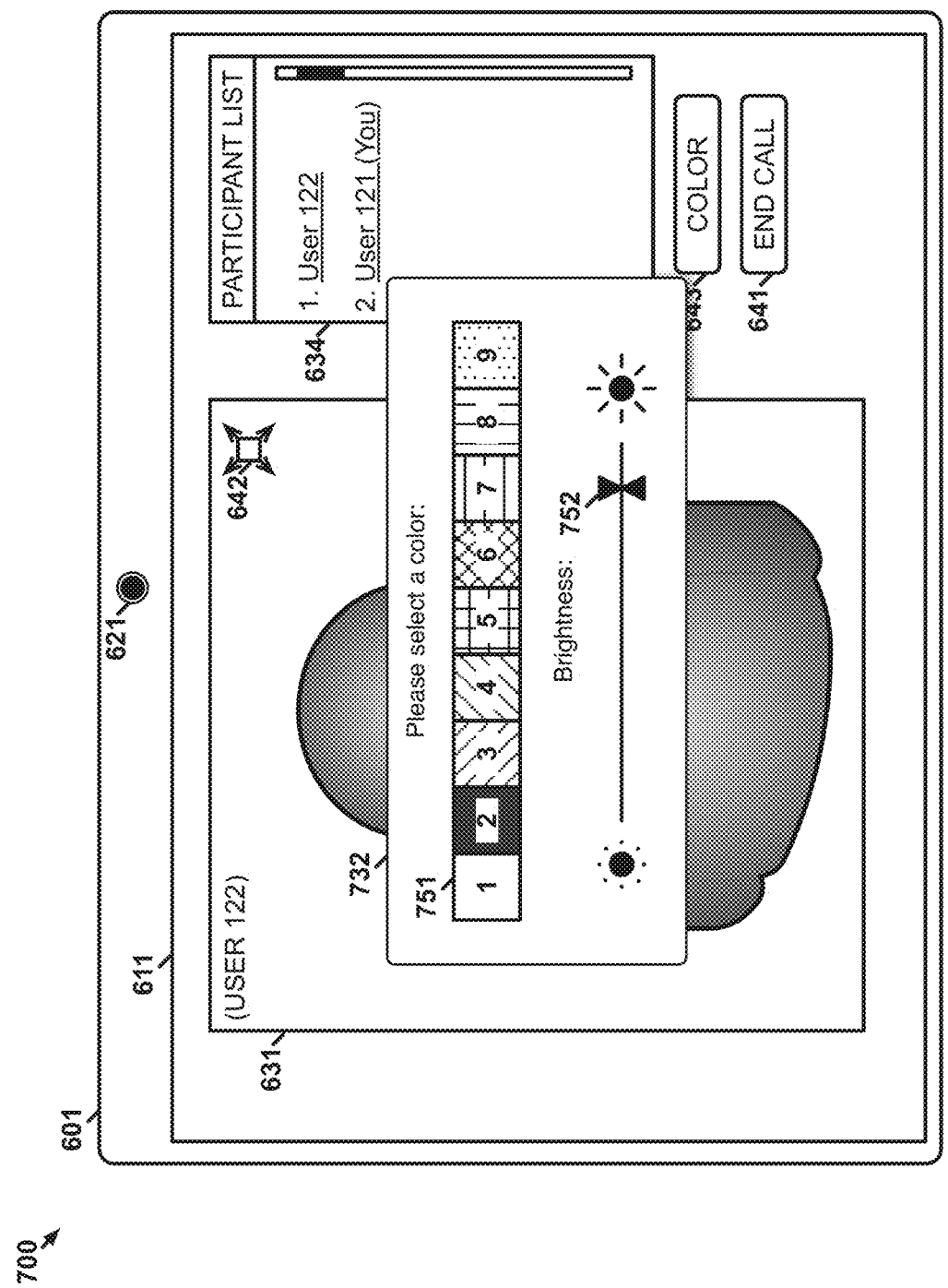
FIG. 7 illustrates an implementation for transmitting a color over a communication session for illumination at an endpoint.

FIG. 7 illustrates implementation 700 for transmitting a color over a communication session for illumination at an endpoint. Implementation 700 is an example of display system 601 after user 121 selects color button 643 while communicating over the video communication session with user 122. The graphical user interface of the client displayed color selection window 732 in response to color button 643 being selected (e.g., clicked on with a mouse cursor, tapped on using a touch screen, etc.). In this example, color selection window 732 includes nine different color options 751 that user 121 may select for transmission in place of the video captured of user 121 by camera 621. Only nine options are provided in this example for simplicity. In other examples, many more color options may be presented to user 121 and alternative manners of displaying the options may be used. Color selection window 732 also includes brightness slider 752. Brightness slider 752 allows user 121 to control the brightness level of display screen 511 at endpoint 102. Thus, rather than user 121 having to ask user 122 to adjust the brightness of display screen 511 manually, the client executing on endpoint 101 may send control messages to endpoint 102 that direct endpoint 102 to adjust the brightness of display screen 511 in accordance with where user 121 positions brightness slider 752. Moving brightness slider 752 to the right results in a brighter screen while moving brightness slider 752 to the left result in a dimmer screen.

Figure 8:
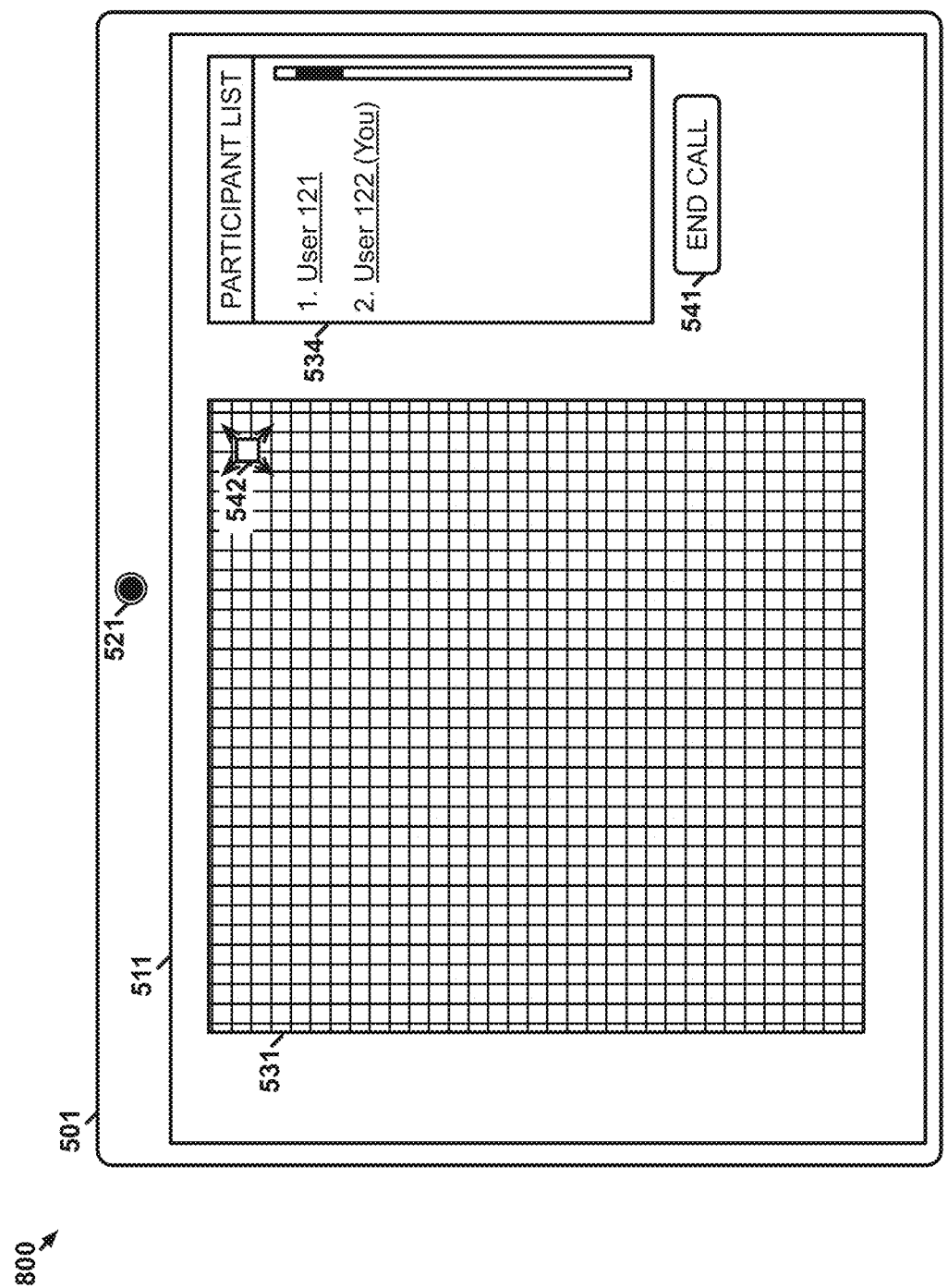
FIG. 8 illustrates an implementation for transmitting a color over a communication session for illumination at an endpoint.

FIG. 8 illustrates implementation 800 for transmitting a color over a communication session for illumination at an endpoint. Implementation 800 is an example of display system 501 after user 121 has selected color option 5 from color options 751. User 121's selection of color option 5 directs endpoint 101 to send video frames filled with color option 5 rather than images captured by camera 621. Since endpoint 102 is displaying the video received from endpoint 101 over the video communication session in video session window 531, video session window 531 now shows only color option 5 rather than video of user 121, as was previously being received from endpoint 101 and shown in video session window 531. While color option 5 is being shown, display screen 511 is also adjusted by endpoint 102 in accordance with brightness slider 752.

Figure 9:
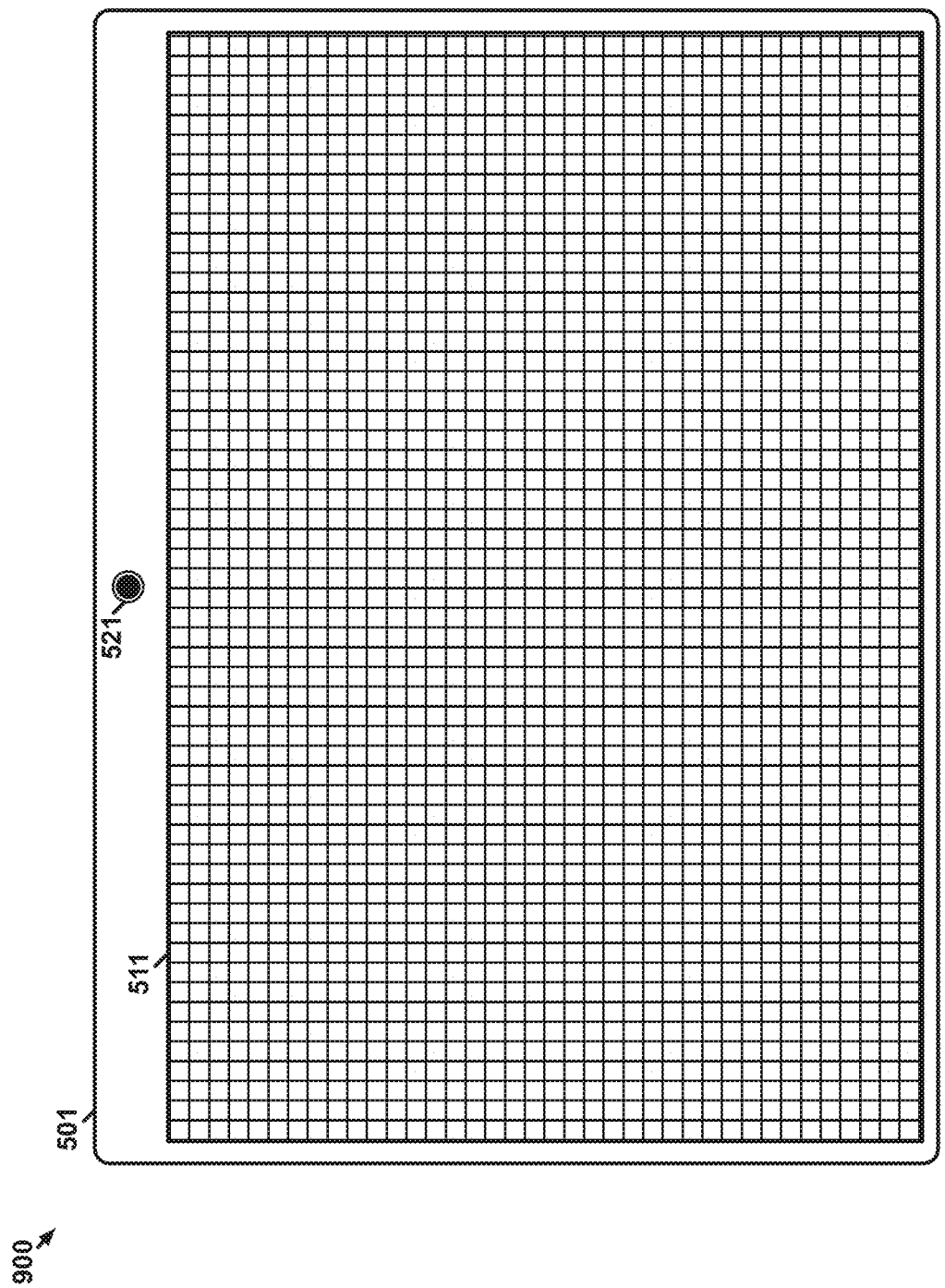
FIG. 9 illustrates an implementation for transmitting a color over a communication session for illumination at an endpoint.

FIG. 9 illustrates implementation 900 for transmitting a color over a communication session for illumination at an endpoint. Implementation 900 is an example of display system 501 after user 122 selects full screen button 542. The video that was presented in video session window 531 now takes up the entirety of display screen 511. Since that video is simply frames of color option 5, color option 5 now fills the entire screen. In other examples, the aspect ratio of the video in video session window 531 may not match the aspect ratio of display screen 511. Black bars may then be used at the top/bottom or sides of display screen 511 to fill in the remaining space or the video may be stretched to fit display screen 511. With the video in full screen, only (or mostly) light in the wavelength(s) of color option 5 is radiating from display screen 511. Other wavelengths from participant list window 534, end call button 541, or any other displayed element on display screen 511 are no longer being radiated so as to interfere with the wavelengths from color option 5.

Figure 10:
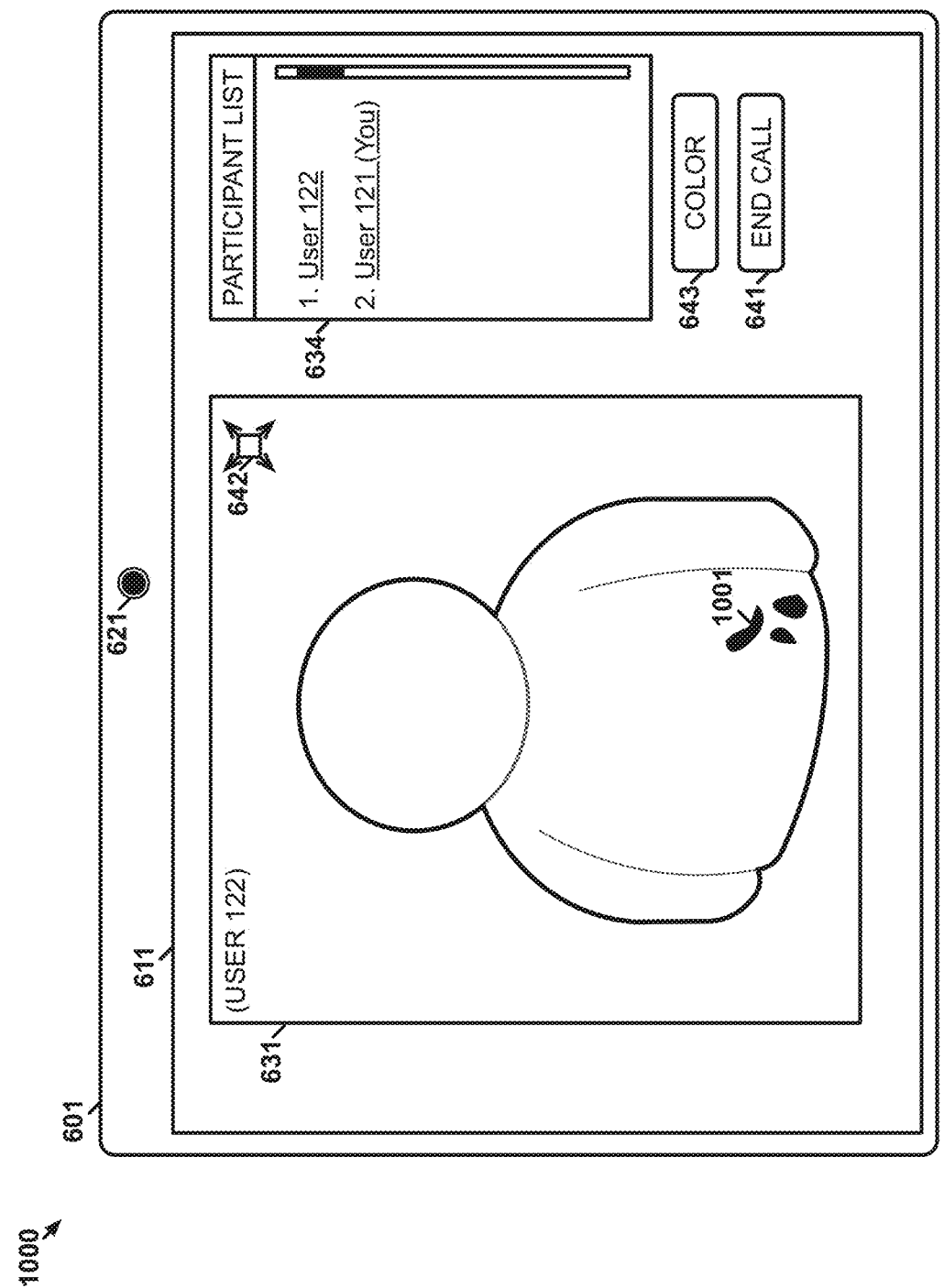
FIG. 10 illustrates an implementation for transmitting a color over a communication session for illumination at an endpoint.

FIG. 10 illustrates implementation 1000 for transmitting a color over a communication session for illumination at an endpoint. Implementation 1000 is an example of display system 601 after user 121 has selected color option 5 through color selection window 732. Specifically, implementation 1000 shows what user 121 sees when viewing video captured by camera 521, which is still being transmitted to endpoint 101 over the video communication session as it was in implementation 600. At this time, however, the light illuminating user 122 has changed from implementation 600 because user 122 is now being illuminated by the full screen display of color option 5, as shown in implementation 900. User 121 may also have requested that user 122 turn off other outside light sources, or move to a darker location, to ensure the light from display screen 511 showing color option 5 is the predominant light source illuminating user 122.

When comparing video session window 631 from implementation 1000 to video session window 631 from implementation 600, user 122 is a different color due to user 122 being illuminated predominantly by color option 5 in implementation 1000. In fact, user 121 is now able to see that user 122 has skin condition 1001 on their torso. The light provided by color option 5 has caused skin condition 1001 standout on user 122 when skin condition 1001 could not be seen at all in implementation 600. If user 121 is a physician, user 121 may then be able to properly treat user 122 for skin condition 1001, which user 121 could not do before when the light illuminating user 122 did not allow for skin condition 1001 to be seen. For instance, skin condition 1001 may be ringworm, a fungal infection that often causes a ring-shaped rash. The affected area tends to be redder (in some cases, only slightly redder) than the adjacent skin. When illuminated by blue light, the visual contrast between a ringworm circle and the adjacent skin can become more evident. In some examples, color option 5 may not allow user 121 to see skin condition 1001 clearly or at all. In those cases, user 121 may open color selection window 732 again to select a different color option from color options 751. The different color option, when included in the video from endpoint 101 and displayed by display screen 511 at endpoint 102, may result in skin condition 1001 being more visible, as shown in implementation 1000.

Once user 121 has seen skin condition 1001, user 121 may direct the client to switch back to sending video of user 121 captured by camera 621 to endpoint 102. For example, user 121 may select color button 643 again and de-select colors option 5 from color selection window 732. The video communication session may then proceed similar to what is shown in implementation 500 and implementation 600 because endpoint 101 is no longer sending color option 5 in the video and endpoint 102 is, therefore, no longer displaying color option 5.

Figure 11:
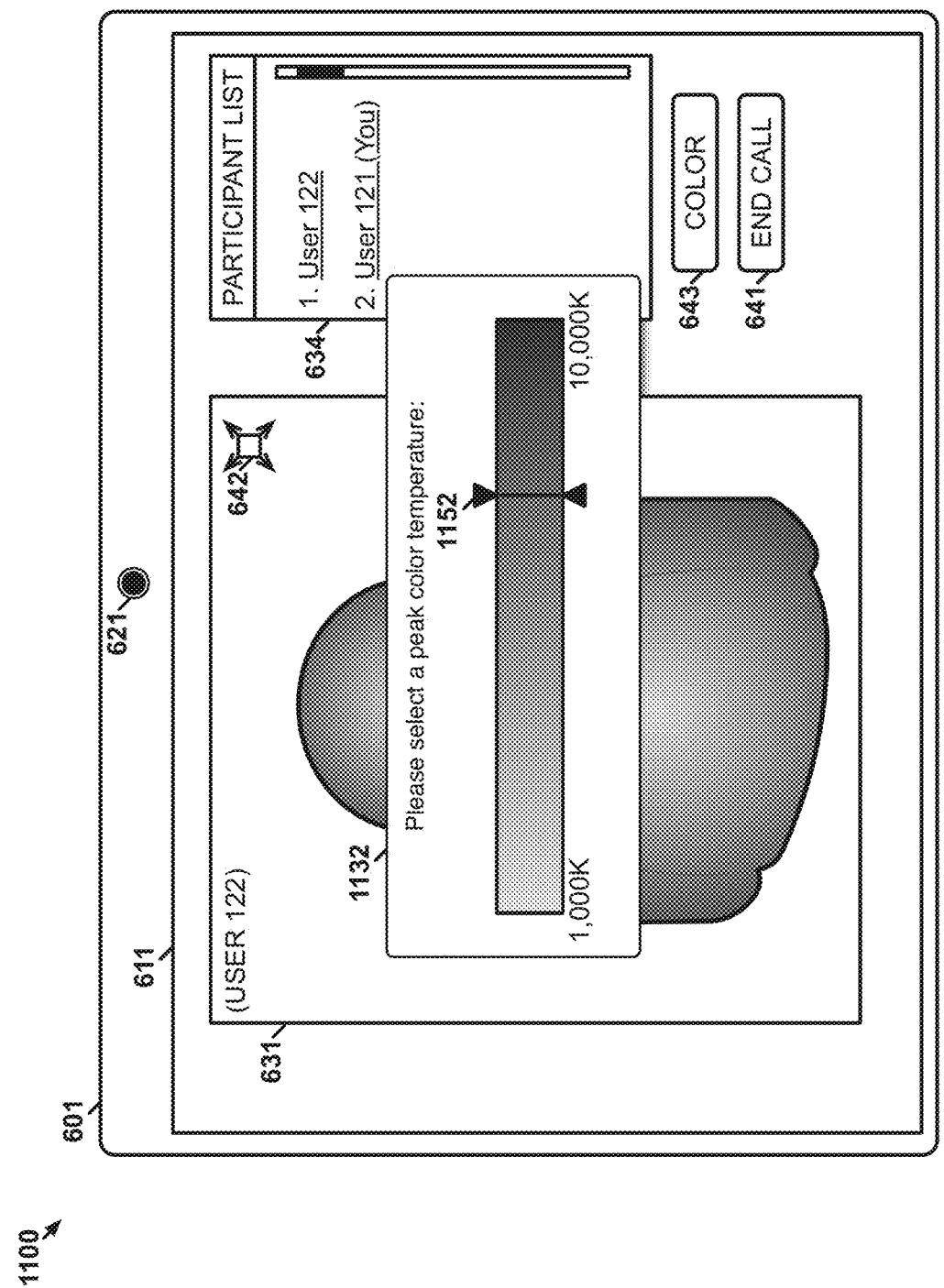
FIG. 11 illustrates an implementation for transmitting a color over a communication session for illumination at an endpoint.

FIG. 11 illustrates implementation 1100 for transmitting a color over a communication session for illumination at an endpoint. Implementation 1100 is an alternative to implementation 700. In implementation 700, after user 121 selects color button 643, color selection window 1132 is displayed. Color selection window 1132 allows user 121 to select a color that produces broad spectrum light based on the peak color temperature of the broad spectrum light. Temperature slider 1152 may be moved left and right by user 121 to select the desired peak color temperature, which may be a temperature between 1,000K and 10,000K in this example. A color that displays the selected peak color temperature at endpoint 102 is then included in the video frames sent to endpoint 102 in place of video captured by camera 621. In some examples, rather than using a slider like temperature slider 1152, endpoint 101 may display an interface where user 121 may select the peak color temperature and specify the shape of the drop-off on either side of that peak. For example, as mentioned above, a pixel is commonly comprised of red, green, and blue sub-pixels and the Red Green Blue (RGB) color model defines an intensity of each sub-pixel (i.e., defined as a number from 0-255, with 0 being off and 255 being brightest) necessary for the pixel as a whole to produce a particular color. User 121 may explicitly provide values for red, green, and blue to create the desired color. In some examples, color selection window 1132 may also include a brightness slider like brightness slider 752. Similarly, color selection window 1132 may provide additional options for color selection. For instance, color selection window 1132 may also present color options 751 and allow user 121 to decide how they want to select a color.

Implementations 500-1100 are only one example of how user 121 may interact with endpoint 101 to send video of a solid color image to endpoint 102 for display. Although, the end result still enables the illumination of user 122 by display screen 511 at endpoint 102. In some examples, user 121 may define the solid color indirectly by indicating what their intended purpose is for the solid color. For example, if user 121 is a physician, then user 121 may indicate to endpoint 101 what medical condition they are looking for on user 122. Endpoint 101 may reference a data structure of medical conditions and respective corresponding colors for viewing those medical conditions to determine a color for the user defined medical condition. Endpoint 101 would then transmit the determined color in the video transmitted to endpoint 102.

FIG. 12 illustrates computing architecture 1200 for transmitting a color over a communication session for illumination at an endpoint. Computing architecture 1200 is an example computing architecture for endpoint 101, although endpoint 101 may use alternative configurations. Other computing systems herein, such as communication session system 103 and endpoint 102 may also use computing architecture 1200. Computing architecture 1200 comprises communication interface 1201, user interface 1202, and processing system 1203. Processing system 1203 is linked to communication interface 1201 and user interface 1202. Processing system 1203 includes processing circuitry 1205 and memory device 1206 that stores operating software 1207.

Communication interface 1201 comprises components that communicate over communication links, such as network cards, ports, RF transceivers, processing circuitry and software, or some other communication devices. Communication interface 1201 may be configured to communicate over metallic, wireless, or optical links. Communication interface 1201 may be configured to use TDM, IP, Ethernet, optical networking, wireless protocols, communication signaling, or some other communication format—including combinations thereof.

User interface 1202 comprises components that interact with a user. User interface 1202 may include a keyboard, display screen, mouse, touch pad, or some other user input/output apparatus. User interface 1202 may be omitted in some examples.

Processing circuitry 1205 comprises microprocessor and other circuitry that retrieves and executes operating software 1207 from memory device 1206. Memory device 1206 comprises a computer readable storage medium, such as a disk drive, flash drive, data storage circuitry, or some other memory apparatus. In no examples would a storage medium of memory device 1206 be considered a propagated signal. Operating software 1207 comprises computer programs, firmware, or some other form of machine-readable processing instructions. Operating software 1207 includes color transmission module 1208. Operating software 1207 may further include an operating system, utilities, drivers, network interfaces, applications, or some other type of software. When executed by processing circuitry 1205, operating software 1207 directs processing system 1203 to operate computing architecture 1200 as described herein.

In particular, color transmission module 1208 directs processing system 1203 to, during a video communication session between a first endpoint operated by a first user and a second endpoint operated by a second user, transmit first video, comprising a solid color image, from the first endpoint to the second endpoint over the video communication session. The first video is prominently displayed at the second endpoint. At the first endpoint, color transmission module 1208 directs processing system 1203 to receive second video from the second endpoint. The second video is captured at the second endpoint while the first video is being displayed at the second endpoint. Color transmission module 1208 further directs processing system 1203 to display the second video to the first user.

The descriptions and figures included herein depict specific implementations of the claimed invention(s). For the purpose of teaching inventive principles, some conventional aspects have been simplified or omitted. In addition, some variations from these implementations may be appreciated that fall within the scope of the invention. It may also be appreciated that the features described above can be combined in various ways to form multiple implementations. As a result, the invention is not limited to the specific implementations described above, but only by the claims and their equivalents.

What is claimed is:

1. A method comprising:
during a video communication session established to exchange real-time user communications between a first endpoint operated by a first user and a second endpoint operated by a second user:
transmitting first video, comprising a solid color image, from the first endpoint to the second endpoint over a video channel of the video communication session for exchange of a video component of the real-time user communications, wherein the first video is prominently displayed at the second endpoint;
at the first endpoint, receiving second video from the second endpoint over the video channel, wherein the second video is captured at the second endpoint while the first video is being displayed at the second endpoint; and
displaying the second video to the first user.

2. The method of claim 1, comprising:
instructing the second endpoint to display the solid color image in a full screen mode.

3. The method of claim 1, comprising:
instructing the second endpoint to adjust a display brightness level.

4. The method of claim 1, comprising:
at the first endpoint, receiving a selection of a color for the solid color image.

5. The method of claim 4, wherein receiving the selection of the color comprises:
displaying a color palette to the first user, wherein the color is selected from the color palette.

6. The method of claim 4, wherein receiving the selection of the color comprises:
at the first endpoint, receiving a selection of a peak color temperature for full-spectrum light.

7. The method of claim 1, wherein the solid color image replaces a video image captured of the first user in the first video.

8. The method of claim 1, comprising:
instructing the second endpoint to disable display color adjustment.

9. The method of claim 1, comprising:
determining a type of video display and a type of video capture component at the second endpoint; and
adjusting display of the second video based on the type of video display and the type of video capture component.

10. The method of claim 1, comprising:
transmitting audio captured of the first user to the second endpoint with the first video.

11. An apparatus comprising:
one or more computer readable storage media;
a processing system operatively coupled with the one or more computer readable storage media; and
program instructions stored on the one or more computer readable storage media that, when read and executed by the processing system, direct the processing system to:
during a video communication session established to exchange real-time user communications between a first endpoint operated by a first user and a second endpoint operated by a second user:
transmit first video, comprising a solid color image, from the first endpoint to the second endpoint over a video channel of the video communication session for exchange of a video component of the real-time user communications, wherein the first video is prominently displayed at the second endpoint;
at the first endpoint, receive second video from the second endpoint over the video channel, wherein the second video is captured at the second endpoint while the first video is being displayed at the second endpoint; and
display the second video to the first user.

12. The apparatus of claim 11, wherein the program instructions direct the processing system to:
instruct the second endpoint to display the solid color image in a full screen mode.

13. The apparatus of claim 11, wherein the program instructions direct the processing system to:
instruct the second endpoint to adjust a display brightness level.

14. The apparatus of claim 11, wherein the program instructions direct the processing system to:
at the first endpoint, receive a selection of a color for the solid color image.

15. The apparatus of claim 14, wherein to receive the selection of the color, the program instructions direct the processing system to:
display a color palette to the first user, wherein the color is selected from the color palette.

16. The apparatus of claim 14, wherein to receive the selection of the color, the program instructions direct the processing system to:
at the first endpoint, receive a selection of a peak color temperature for full-spectrum light.

17. The apparatus of claim 11, wherein the solid color image replaces a video image captured of the first user in the first video.

18. The apparatus of claim 11, wherein the program instructions direct the processing system to:
instruct the second endpoint to disable display color adjustment.

19. The apparatus of claim 11, wherein the program instructions direct the processing system to:
determine a type of video display and a type of video capture component at the second endpoint; and
adjust display of the second video based on the type of video display and the type of video capture component.

20. One or more computer readable storage media having program instructions stored thereon that, when read and executed by a processing system, direct the processing system to:
during a video communication session established to exchange real-time user communications between a first endpoint operated by a first user and a second endpoint operated by a second user:
transmit first video, comprising a solid color image, from the first endpoint to the second endpoint over a video channel of the video communication session for exchange of a video component of the real-time user communications, wherein the first video is prominently displayed at the second endpoint;
at the first endpoint, receive second video from the second endpoint over the video channel, wherein the second video is captured at the second endpoint while the first video is being displayed at the second endpoint; and
display the second video to the first user.

* * * * *